United States Patent [19]

Ulich

[11] Patent Number: 5,013,917
[45] Date of Patent: * May 7, 1991

[54] IMAGING LIDAR SYSTEM USING NON-VISIBLE LIGHT

[75] Inventor: Bobby L. Ulich, Tuscon, Ariz.

[73] Assignee: Kaman Aerospace Corporation, Bloomfield, Conn.

[ * ] Notice: The portion of the term of this patent subsequent to Aug. 29, 2006 has been disclaimed.

[21] Appl. No.: 256,778

[22] Filed: Oct. 12, 1988

Related U.S. Application Data

[63] Continuation-in-part of Ser. No. 216,087, Jul. 7, 1988, and a continuation-in-part of Ser. No. 216,341, Jul. 7, 1988, Pat. No. 4,862,257.

[51] Int. Cl.$^5$ ............................................. H04N 7/18
[52] U.S. Cl. ................................... 250/330; 358/95; 358/113; 250/332
[58] Field of Search ........... 250/330, 332, 334, 370.08; 358/113, 95

[56] References Cited

U.S. PATENT DOCUMENTS

| | | |
|---|---|---|
| 2,541,374 | 2/1951 | Morton . |
| 3,305,633 | 2/1967 | Chernoch .......................... 358/113 |
| 3,426,207 | 2/1969 | Fried et al. . |
| 3,467,773 | 9/1969 | Heckman, Jr. . |
| 3,566,021 | 2/1971 | Jakes, Jr. . |
| 3,670,098 | 6/1972 | Korpel . |
| 4,030,831 | 6/1977 | Gowrinathan ..................... 356/109 |
| 4,174,524 | 11/1979 | Moran ................................... 358/95 |
| 4,298,280 | 11/1981 | Harney ................................ 250/332 |
| 4,639,590 | 1/1987 | butterwick .................. 250/213 VT |
| 4,757,200 | 7/1988 | Shepherd ............................ 250/332 |
| 4,862,257 | 8/1989 | Ulich ..................................... 358/95 |

Primary Examiner—Carolyn E. Fields
Attorney, Agent, or Firm—Fishman, Dionne & Cantor

[57] ABSTRACT

A system is presented for the remote detection and imaging of objects at night. In accordance with the present invention, a laser is used to generate short pulses of infrared light with pulse widths on the order of nanoseconds. The laser light is expanded by optics and projected at the target scene. An intensified CCD (charge coupled device) camera is electronically shuttered after an appropriate time delay such that the image formed by the camera is composed of infrared light backscattered by the target from a range of r.

32 Claims, 2 Drawing Sheets

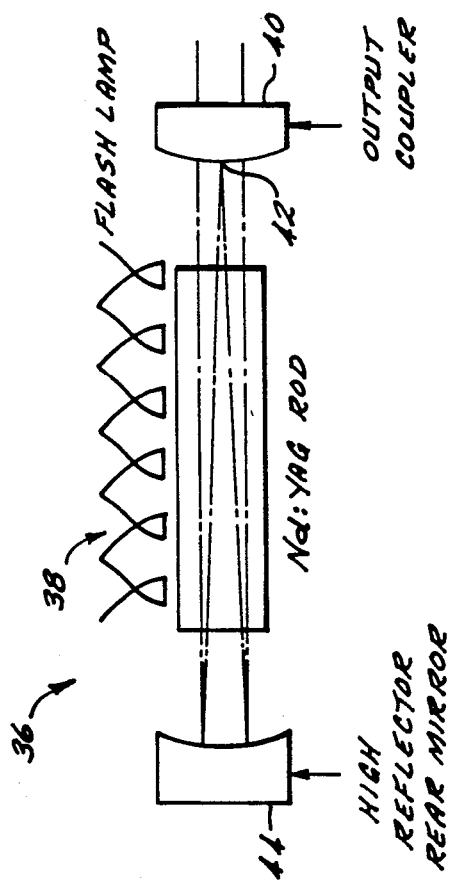
FIG. 3
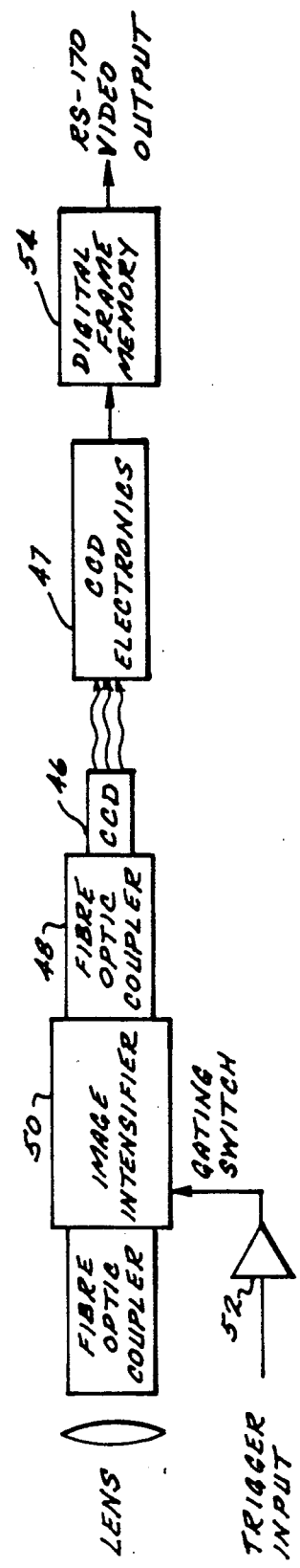
FIG. 2
FIG. 4

IMAGING LIDAR SYSTEM USING NON-VISIBLE LIGHT

BACKGROUND OF THE INVENTION

This invention relates generally to a method and apparatus for remote imaging of objects at night. More particularly, this invention relates to a method for detecting and imaging objects at night or where atmospheric propagation of visible light is severely hampered by fog, dust, smoke, haze, snow and the like using a novel infrared imaging lidar (light detection and ranging) system.

There is a continuing need to develop methods of detecting targets at night (e.g. night vision) from remote locations (e.g. airborne or from an Earth satellite) and over relatively short time periods. This is of particular importance in the case of certain military applications where covert night time surveillance has consistently been critical. Presently, infrared night vision devices are known. However, these known, prior infrared devices suffer from certain drawbacks and deficiencies including lack of sensitivity and resolution at long ranges.

In addition to providing improved covert night vision, there is a continuing need for remote detection and imaging systems for daytime use in conditions where atmospheric propagation of visible light is severely hampered by fog, dust, smoke, haze, snow and the like.

Unfortunately, no workable system for the remote detection and imaging of objects at night (or objects obscured by other media such as ice, snow, fog, smoke, and dust) is known which obtains accurate and precise imaging over short time periods and from a variety of remote platforms including aircraft, ships and submarines.

SUMMARY OF THE INVENTION

The above-discussed and other drawbacks and deficiencies of the prior art are overcome or alleviated by the novel system of the present invention for remote detection and imaging of objects at night (or in the daytime when obscured by smoke, dust, snow and the like). In accordance with the present invention, a laser is used to generate short pulses (e.g. less than approximately 100 ns) of infrared (e.g. non-visible) light. The laser light is expanded by optics and projected toward the target scene or object. An intensified CCD (charge coupled device) camera sensitive to the laser wavelength is electronically shuttered after an appropriate time delay (from the timing electronics) such that the image formed by the camera is composed of light backscattered or reflected by the target from the target scene.

Timing between the ICCD camera and the pulsed laser is an important feature of this invention. Preferably, a glint detector composed of a fast photodiode and a pulse discriminator is used to control timing. The glint detector detects the leading edge of the backscattered laser pulse, which is then amplified and converted to a digital pulse which then is delivered into the timing electronics module. In this module, a clock is started and when a period nearly equal to the laser pulse repetition frequency (PRF) is reached, the camera electronic shutter is opened. Thus, the camera is gated on one pulse after the glint detector detects a target return.

BRIEF DESCRIPTION OF THE DRAWINGS

Referring now to the drawings, wherein like elements are numbered alike in the several FIGURES:

FIG. 2 is a schematic diagram of the pulsed laser used in the system of FIG. 1;

FIG. 3 is a diagram of a spatial profile of a single pulse from the laser of FIG. 2; and FIG. 4 is a schematic diagram of the CCD camera used in conjunction with the system of FIG. 1.

DESCRIPTION OF THE PREFERRED EMBODIMENT

Figure 1:
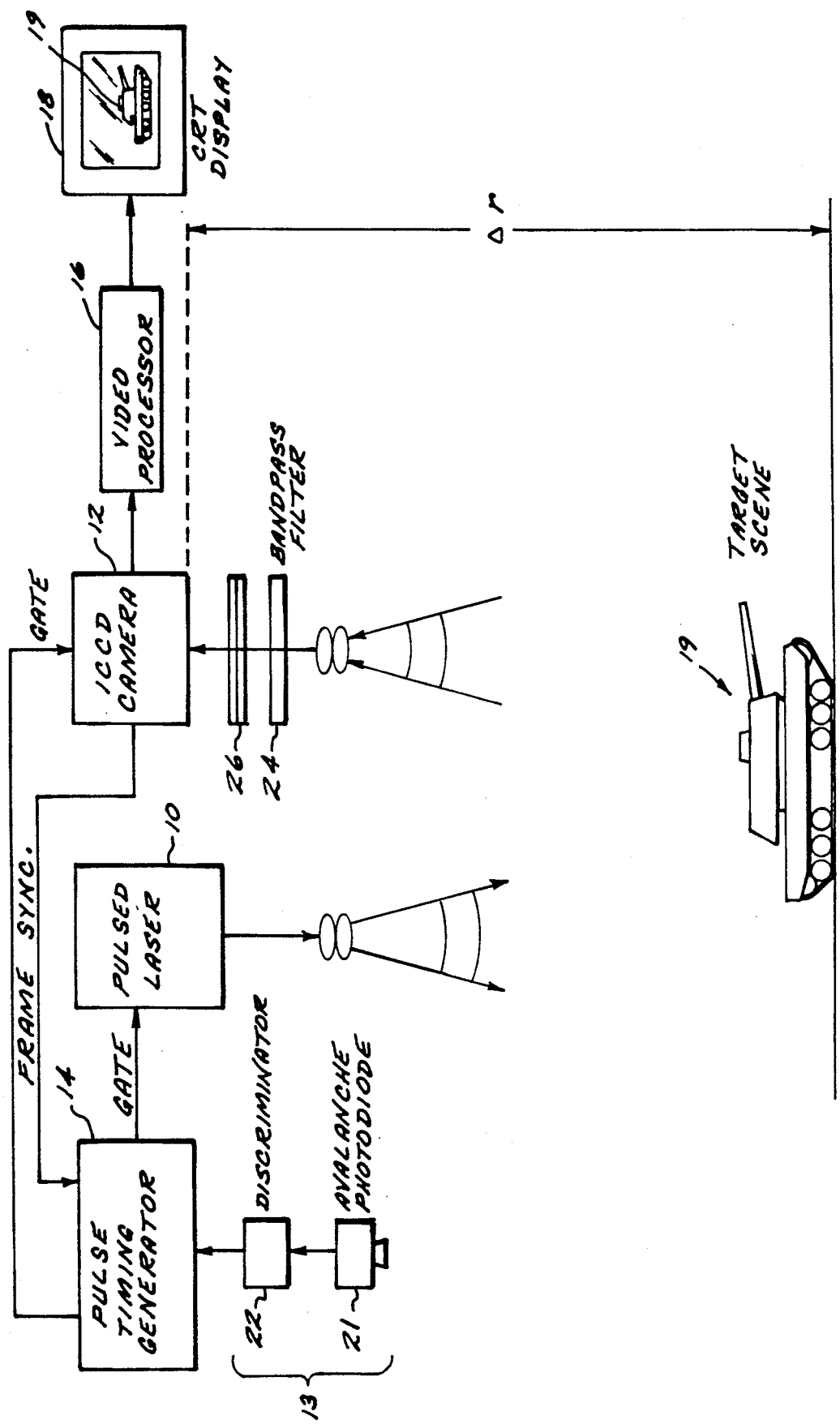
FIG. 1 is a schematic block diagram of the system for detecting and imaging targets at night in accordance with the present invention.

The present invention relates to a remote sensing unit for detecting and imaging targets and other objects at night and in the daytime in conditions where atmospheric propagation of visible light is severely hampered by fog, dust, smoke, haze, snow and the like. Referring to FIG. 1, the present invention generally comprises a pulsed laser 10 which operates at a wavelength in the infrared which is invisible to the human eye (more than 900 nm), a fast gated television camera 12, a glint detector 13, timing control electronics 14 for controlling laser 10 and camera 12, video processing unit 16 and cathode ray tube (CRT) unit 18. When a non-visible light pulse (e.g. infrared) is emitted from laser 10, the light is passed through a negative focal length lens 20 to expand the laser beam into a cone which illuminates a spot at the target scene 19. The shutter on camera 19 is opened briefly after an appropriate delay time such that the image formed by the camera and lens is composed of light backscattered or reflected by the target scene. The signals from the camera are then processed in video processing unit 16 and displayed on a cathode ray tube 18. In the particular example shown in FIG. 1, the target imaged is a tank 19.

The timing electronics 14 contains a master oscillator which fires the laser 10 during vertical flyback of the camera video output. As a result, the laser pulse repetition frequency (PRF) will be 60 Hz or an even submultiple thereof. Thus, for a field rate camera (e.g. 60 Hz readout, non-interlaced), the laser pulse frequency can be 60 Hz, 30 Hz, 15 Hz, etc. For frequencies less than 60 Hz, blank (black) fields will occur between target images. If desired, a video frame store memory can be used in units 12 or 16 to repeat the target images thus avoiding the intensity flicker in video display unit 18 which may be distracting to the viewer.

Glint detector 13 contains a fast photodiode 21 and a pulse discriminator 22. The leading edge of the backscattered laser pulse is detected, amplified, and converted to a digital pulse signal which goes into the timing electronics module 14. In module 14, a clock is started, and when a period nearly equal to the PRF period is reached, the camera electronic shutter is opened. Thus, camera 12 is gated on one pulse after glint detector 13 detects a target return. This delay of one pulse is necessary since the electronic propagation delays in glint detector 13, timing electronics module 14, camera 12, and the various interconnecting cables are longer than the desired exposure times. An advantage of this method is that varying target ranges are accommodated with negligible errors. Thus, the lidar platform can be nonstationary (for example, airborne).

The camera exposure time (gate width) $\tau$ is related to the range difference $\Delta r$ by:

$$\tau = \left[\frac{2n}{C}\right]\Delta r \quad (1)$$

where C is the velocity of light in a vacuum; and n is the index of refraction of the infrared light in the propagation medium (generally air, so $n \approx 1$). Thus, for a $\Delta r$ of 1000 feet:

$$\tau = [2 \times 1/(3 \times 10^8 \times 1\ ft./0.3048)]1000 \approx 2\ ms.$$

Assuming that the reflected photons are back scattered uniformly over $2\pi$ steradians by opaque targets, the detected signal strength S is given by:

$$S = \frac{E\lambda\Gamma\eta_\epsilon A}{2\pi r^2 hCN} \quad (2)$$

where
E = laser pulse energy (J)
$\Gamma$ = target reflectance (dimensionless)
r = target range (m)
N = number of pixels in TV camera image (dimensionless)
$\lambda$ = laser wavelength (m) (in vacuum)
h = planck's constant ($6.626 \times 10^{-34}$ J s)
A = effecting collecting area of camera lens (m$^2$)
C = velocity of light ($2.997q \times 10^8$ m s$^{-1}$)
S = number of photoelectrons detected per pixel per pulse
$\eta_\epsilon$ = camera photocathode quantum efficiency In Equation (2) the solid angles of the laser beam expander and the camera lens are assumed equal If shot noise dominates other noise processes, the signal-to-noise ratio (SNR) in a pixel is given by:

$$SNR = S^{\frac{1}{2}} \quad (3)$$

Thus, for
E = 1 J
$\Gamma$ = 0.1
N = 400 × 500 = 2 × 10$^5$
$\lambda$ = 1.06 × 10$^{-6}$ m
A = 0.05 m$^2$
$\eta_\epsilon$ = 0.05
then
S = 1.06 × 10$^9$/r$^2$
SNR = 3.3 × 10$^4$/r
and where
r = 1000 m
SNR = 33.0
and where
r = 10,000 m
SNR = 3.3

Accordingly, very dark objects may be imaged using the present invention out to r = 10 km and reflective targets (r = 0.8) may be imaged out to 28 km with SNR being approximately greater than or equal to 3.3.

The present invention as depicted in FIG. 1 will now be described in much greater detail. It will be appreciated that the following description is of a preferred embodiment and that the particular component models, manufacturers and similar details are by example only.

Pulsed Laser

The preferred laser system used with the system of this invention is a Spectra Physics DCR-4 pulsed Nd:YAG laser which emits short, but very bright pulses of infrared light at 1064 nm.

As shown in FIG. 2, the pulsed Nd:YAG laser uses a diffraction-coupled resonator 36 which provides high energy, good stability, good beam quality, and a high degree of spatial coherence. The Nd:YAG rod is optically excited through the use of a high voltage flash lamp 38. The output coupler (front lens 40) has a single high reflectivity dot 42 located in the center of the convex substrate. The rear mirror 44 is a concave high reflector which collimates the beam and will compensate for the thermal lensing of the Nd:YAG rod. The collimated beam passes through the rod on its exit path, and the light diffracts around the edge of the dot located on the front output coupler. This produces a characteristic "donut" spatial profile, as shown in FIG. 3. A Q-switch (Pockels cell) is used in conjunction with a Marx bank and a quarter-wave plate to regulate the temporal width of the pulse. The initial storage of energy is accomplished by the quarter-wave plate. The light pulse is formed by applying a very high speed, high voltage waveform to the Pockels cell.

Typical pulse lengths are less than or equal to 100 ns. Thus, the duty cycle is very low and for modest average power level the peak power will be very high. As an example, a Spectra Physics DCR-4 laser preferably has a pulse length of about 10 ns (slow mode) and an average power of about 15 W at 15 Hz PRF. Each pulse contains 1 joule of energy and the peak power is 10$^8$ W.

The laser is externally cooled through the use of a self-contained cooling system. In addition, all cavities are air purged. The cooling system, electronics and purge system are housed in a separate power supply which is rack mountable. All cables, air and water lines are connected to the laser head and power supply by a 10 ft. umbilical cord. The laser can be operated at 208 V, 60 Hz, single phase power, or with 120/220 V power.

Cameras

The preferred system of the present invention uses a Marco Scientific Model 201 Camera as shown in FIG. 4. The image sensor 46 used in this camera is a Thompson CSF model TH-7882-FO charge coupled device (CCD) driven by CCD electronics package 47. This particular CCD features a fiber optic window 48 which is used to couple the sensor to an intensifier tube. The intensifier tube 50 serves as both a light amplifier and an ultrafast shutter driven by a high voltage amplifier 52. This camera also includes a built-in digital frame store/-scan converter 54 whose output is converted to an RS170 analog signal for additional image processing and for display on a standard video monitor 18.

The intensifier tube 50 is a DEP Model XX1420 with two gain stages. The first is a Gen II type intensifer with a microchannel plate (MCP); the second is a Gen I proximity focused diode. Net luminance gain is nominally 100,000. The tube's S-20 photocathode defines the spectral response for the entire camera and establishes the quantum efficiency limitation at about 7%. The anode phosphor on the back end of the tube is fiber-optically coupled to the CCD sensor. A control switch on the camera body allows selection of an intensifier gate width of 10, 20 or 40 ns. This is equivalent to an exposure setting for the camera.

The CCD being used is a novel frame transfer device. Normally in prior known RS170 compatible frame transfer devices, an image is integrated on the image area and then shifted to an adjacent storage area of the CCD. With each new TV line, the horizontal register shifts the stored information out. Since normal TV operates in an interlaced mode, a phase shift between the odd and even field allows the CCD to operate in a kind of interlaced readout mode. In these prior devices, the storage area occupies half the sensor and only half the elements actually integrate light. It is important to note that the sensor being used in the Model 201 Camera of this invention uses the entire area of the chip for light integration and, as such, is generally not compatible with standard RS170 operation. As will be discussed hereinafter, there are marked benefits of having a 100% sensitivity chip area in terms of ultimate system sensitivity.

The CCD features 568 lines by 382 columns of 23 micrometer square pixels in a contiguous format. Of this array, only a nominal 512 lines are used to achieve the correct aspect ratio for display on a standard video monitor (4:3 aspect ratio). As previously stated, the CCD being used here is generally not compatible with standard RS170 video output. In the infrared imaging lidar system of the present invention, the following sequence takes place to achieve a suitable video output:

(1) The CCD is undergoing continual downward shifting of the horizontal shift registers to clear away any dark current build-up.

(2) An external trigger signal turns on the intensifier to start an exposure. Upon receipt of this signal the CCD shift mode is interrupted and for the next 3.2 ms, the CCD is in the integration mode. The 3.2 ms allows the phosphor persistence to decay to less than 5% after the short (20–40 ns) exposure, thus serving to optimize SNR.

(3) At the end of the 3.2 ms, the CCD is switched into the readout mode where the accumulated charge for each pixel is read into the digital frame store. In addition to the digitizing of the data, a format manipulation occurs in the frame store in which the sensor image is effectively rotated 90 degrees (i.e., columns are converted to rows and vice-versa). The 3:4 aspect ratio of the sensor now maps properly onto the 4:3 aspect ratio of a standard video monitor. This entire process takes 8.2 msec.

(4) Once readout into the frame store is complete, the CCD reverts back to the continuous shift mode to eliminate dark current build-up until the next intensifier trigger is received.

A D/A converter outputs the frame store information as a composite video field. This field gets repeated at 60 Hz until the frame store is updated. Alternating fields in the composite video, although identical, get interlaced in the conventional manner. Each time the signal is received to begin an integration and readout on the sensor, a single blank field is generated on the composite video. Note that the total time for integration and readout (3.2+8.2 ms) is within a field interval (16.67 ms). It should be noted that the video field consists of 190 lines. After the 190 lines, the frame converter switches to a standard TV display mode and displays the remaining lines as black.

Several of the camera control features have already been mentioned. These include the external gating trigger via an input on the camera body and the gate width control switch (10, 20 or 40 ns). Also found on the camera body are three outputs. The Gain Monitor shows a divided down replica of the high voltage gating pulse going to the intensifier tube. The Frame Synch out is a 1.98 μs wide TTL negative pulse indicating the start of an odd field in the composite video, and thus occurring at 30 Hz. The Field Synch out is a 1.33 ms TTL negative pulse indicating the retrace blank (or vertical flyback) occurring between each field of the composite video at 60 Hz. A rack mountable power supply provides the low voltage power of the camera electronics as well as the high voltages needed for the two stages of the intensifier tube. There is potentiometer control for manual control of the high voltages on the power supply front panel. This is used to vary and monitor gain through the tube. In a preferred embodiment, an automatic gain control circuit is used to automatically correct gain at field rate.

For an intensified CCD camera with a diagonal dimension of d, a lens of focal length F has an angular field of view diameter $\theta$ given by:

$$\tan \theta/2 = \frac{d}{2F} \tag{4}$$

which is approximated for small angles as:

$$\theta \approx d/f \tag{5}$$

For a circular, unobscured aperture of diameter D, the lens collecting area is given by:

$$A = \pi D^2/4 \tag{6}$$

and the lens focal ratio F is given by:

$$F = f/D \tag{7}$$

For a target field of view of linear dimension L at range r, the angular field $\theta$ is given by:

$$\theta = 2 \operatorname{Tan}^{-1}\left[\frac{L}{2r}\right] \tag{8}$$

and from Equation 4 above we also have:

$$\theta = 2 \operatorname{Tan}^{-1}\left[\frac{d}{2F}\right] \tag{9}$$

so that $$\frac{L}{r} = \frac{d}{F} \tag{10}$$

For L=200 m at r=5000 m, and with d=14 mm, f=0.35 m. With F=1.0, D=0.35 m and A=0.096 m . Thus a "fast" optical lens system is desired in order to maximize the collecting area for a given field of view.

For a long focal length lens on an airborne platform, it may be necessary to stabilize the line of sight by gyroscopically stabilizing the optical mounting platform or to otherwise control the line of sight pointing axis by the use of steering mirrors. Blurring during an exposure will generally be insignificant because of the very short exposure time. However, significant target image motion may occur between pulses which will degrade the image quality seen by the operator on the video display unit.

Referring to FIG. 1, the timing control schematic for the system of this invention is shown. The principal elements in the overall timing scheme are the camera 12 and a Standard Research Model DG535 Digital Delay Generator 14. The 30 Hz Frame Synch signal from the camera is divided down to 15 Hz and used to trigger the laser (see FIG. 1). Recall that the Frame Synch signal occurs at the beginning of the odd field interval in the camera composite video. A laser output pulse is generated roughly 250 μs after the trigger input signal. The laser glint return from the target scene is detected by an Antel Optronics ARX - SA high speed avalanche photodetector 20. Given the expected altitude of the platform in an operational system, glint detection will generally be on the order of 30 μs after the laser pulse output. The photodetector signal is conditioned through a Modern Instrument Technology F-100T Pulse Pre-Amp and Noise Discriminator 22. The threshold of the F-100T is set above the noise level and in the linear region of the signal source level. A 100 ns wide TTL pulse is output when the signal source reaches the threshold level. This TTL pulse triggers Stanford delay unit 14. This pulse timing generator 14 is the primary timing control for the system and is used to trigger intensifier gating for the CCD camera 12. It is set for a delay of (66 2/3 ms - system delays). Hence, the camera is actually triggered on the previously detected glint pulse. System delays will be on the order of 130 ns (i.e. 40 ns propagation delay of the camera gate, 85 ns propagation delay of the Stanford, and 5 ns for other delays such as cable lengths, etc.). These delays can be accurately measured and should have jitter specifications $\leq 1$ ns. The Stanford is capable of delaying a pulse very accurately for many milliseconds with its stable internal timebase oscillator. The RMS jitter specification is defined as: (50ps+delay X 10E-8). For example, delays on the order of 70 ms have a RMS jitter spec of 0.7 ns. Once the system is calibrated, the delay is independent of distance from the target (i.e., the system automatically tracks changing target range). However, this requires that the event be initiated accurately to within $\leq 2$ ns at 15 Hz rep rate. This is possible only if the Frame Synch of the CCD camera is stable to $\leq 1$ ns and the laser jitter referenced from TTL input is stable to $\leq 1$ ns.

At the beginning of every other odd video field, an event is initiated (i.e., the laser is pulsed at 15 Hz). The laser return is detected and the round trip pulse transit time is taken into account in gating the cameras on at the desired time for a given target range on the next event (laser pulse). This gating will always occur during the first 100 μs of alternating odd video field intervals. Then sensor integration and readout occurs for 3.2 ms and 8.2 ms, respectively. During this field interval when intensifier gating, sensor integration, and sensor readout occur, an entire blank composite video field is read out of the camera's frame store memory. The ensuing three video fields are identical presentations of the captured event as read from the camera framestore. During this time, the camera waits for a trigger to initiate a new event and continually clears dark current from the CCD. The next trigger always occurs near the beginning of the fourth successive composite video field interval and the cycle is repeated.

Video Processor

A RS 170 signal from the intensified CCD camera is first patched through a monochrome video monitor (Cohu Model 9029B/2R) and is then fed into the inputs of the image processor. The image processor 16 is a computer which digitizes each pixel in the image and, based on the intensities measured derives a video image for each pixel and displays it as a monochrome intensity or as a colorized (false color) picture.

Camera Lens Optics

The system of this invention may optionally contain certain small optical filters including bandpass filter 24 and polorazing filters 26. A narrow bandpass filter may be placed in front of the camera lens to avoid detecting other emissions such as sunlight, moonlight, active illumination sources at the target scene, etc., although in general, there may be no advantage in doing this.

While preferred embodiments have been shown and described, various modifications and substitutions may be made thereto without departing from the spirit and scope of the invention. Accordingly, it is to be understood that the present invention has been described by way of illustrations and not limitation.

What is claimed is:

1. A method of detecting and imaging an object at night or where atmospheric propagation of visible light is severely hampered by fog, dust, smoke, haze or snow including the steps of:
   selectively generating pulses of non-visible light;
   projecting said pulses of non-visible light at an object at night or where atmospheric propagation of visible light is severely hampered by fog, dust, smoke, haze or snow;
   detecting said pulses of light reflected back from said object after a time delay corresponding to the round-trip propagation time of said light pulses to and from said object using at least one camera means;
   detecting the leading edge of light reflected back from said object using glint detection means;
   gating said at least one camera means on one pulse after said glint detection means detects the leading edge of the reflected light; and
   converting the detected pulses of non-visible light to a video image of said object.

2. The method of claim 1 wherein:
   said pulses of non-visible light are generated by pulsed laser means.

3. The method of claim 2 wherein:
   said pulsed laser means comprises a pulsed Nd:YAG laser.

4. The method of claim 1 wherein:
   said pulses comprise pulse widths of less that about 100 nanoseconds.

5. The method of claim 1 including:
   expanding said generated pulses of light by directing said pulses through optical means.

6. The method of claim 2 wherein:
   said pulses of non-visible light are in the infrared wavelength.

7. The method of claim 1 including:
   filtering the reflected pulses of light.

8. The method of claim 7 including:
   using bandpass filter means to discriminate said pulses of light from background light sources.

9. The method of claim 1 wherein:
   said at least one camera means includes an intensified charge coupled device (CCD) sensor.

10. The method of claim 9 wherein said at least one camera means further includes:
    fiber optic window means; and
    intensifier tube means, said fiber optic window means coupling said CCD sensor to said intensifier tube means to define said intensified CCD sensor.

11. The method of claim 1 including:

displaying said video image on cathode ray tube means.

12. The method of claim 2 wherein the detected signal strength S is given by: where $$S = \frac{E\lambda\Gamma\eta_\epsilon A}{2\pi r^2 hCN}$$

E = laser pulse energy (J)
Γ = target reflectance (dimensionless)
r = target range (m)
N = number of pixels in TV camera image (dimensionless)
λ = laser wavelength (m) (in vacuum)
h = planck's constant ($6.626 \times 10^{-34}$ J s)
A = effective collecting area of camera lens (m²)
C = velocity of light ($2.9971 \times 10^8$ m s$^{-1}$)
S = number of photoelectrons detected per pixel per pulse
$\eta_\epsilon$ = camera photocathode quantum efficiency 13. The method of claim 12 wherein the signal-to-noise ratio (SNR) in a pixel is given by:

$$SNR = S^{\frac{1}{2}}$$

14. An apparatus for detecting and imaging an object at night or where atmospheric propagation of visible light is severely hampered by fog, dust, smoke, haze or snow comprising:
generating means for selectively generating pulses of non-visible light;
projecting means for projecting said pulses of non-visible light at an object at night or where atmospheric propagation of visible light is severely hampered by fog, dust, smoke, haze or snow;
at least one camera means for detecting said pulses of light reflected back from said object after a time delay corresponding to the round-trip propagation time of said light pulses to and from said object;
glint detection means for detecting the leading edge of light reflected back from said object;
gating means for gating said at least one camera means on one pulse after said glint detection means detects the leading edge of the reflected light; and
converting means for converting the detected pules of non-visible light to a video image of said object.

15. The apparatus of claim 14 wherein:
said generating means comprises pulsed laser means.

16. The apparatus of claim 15 wherein:
said pulsed laser means comprises a pulsed Nd:YAG laser.

17. The apparatus of claim 14 wherein:
said pulses comprise pulse widths of less than about 100 nanoseconds.

18. The apparatus of claim 15 wherein:
said pulses of non-visible light are in the infrared wavelength.

19. The apparatus of claim 14 including:
means for expanding the generated pulses of light by directing said pulses through optical means.

20. The apparatus of claim 14 including:
means for filtering the reflected pulses of light.

21. The apparatus of claim 20 wherein:
said filtering means comprises bandpass filter means.

22. The apparatus of claim 14 wherein:
said at least one camera means includes an intensified charge coupled device (CCD) sensor.

23. The apparatus of claim 22 wherein said at least one camera means further includes:
fiber optic window means; and
intensifier tube means, said fiber optic window means coupling said CCD sensor to said intensifier tube means to define said intensified CCD sensor.

24. The apparatus of claim 14 including:
means for visually displaying said video image.

25. The apparatus of claim 14 wherein the detected signal strength S is given by:

$$S = \frac{E\lambda\Gamma\eta_\epsilon A}{2\pi r^2 hCN}$$

where
E = laser pulse energy (J)
Γ = target reflectance (dimensionless)
r = target range (m)
N = number of pixels in TV camera image (dimensionless)
λ = laser wavelength (m) (in vacuum)
h = planck's constant ($6.626 \times 10^{-34}$ J s)
A = effective collecting area of camera lens (m²)
C = velocity of light ($2.9971 \times 10^8$ m s$^{-1}$)
S = number of photoelectrons detected per pixel per pulse
$\eta_\epsilon$ = camera photocathode quantum efficiency 26. The apparatus of claim 24 wherein the signal-to-noise ratio (SNR) in a pixel is given by:

$$SNR = S^{\frac{1}{2}}$$

27. The apparatus of claim 14 wherein said glint detection means comprises:
fast photodiode means; and
pulse discriminator means operatively connected to said fast photodiode means.

28. A method of detecting and imaging an object at night or where atmospheric propagation of visible light is severely hampered by fog, dust, smoke, haze or snow including the steps of:
selectively generating pulses of non-visible light;
projecting said pulses of non-visible light at an object at night or where atmospheric propagation of visible light is severely hampered by fog, dust, smoke, haze or snow;
detecting said pulses of light reflected back from said object after a time delay corresponding to the round-trip propagation time of said light pulses to and from said object wherein glint detection means is used to detect the leading edge of light reflected back from said object; and
converting the detected pulses of non-visible light to a video image of said object.

29. A method of detecting and imaging an object at night or where atmospheric propagation of visible light is severely hampered by fog, dust, smoke, haze or snow including the steps of:
selectively generating pulses of non-visible light;
projecting said pulses of non-visible light at an object at night or where atmospheric propagation of visible light is severely hampered by fog, dust, smoke, haze or snow;
detecting said pulses of light reflected back from said object using at least one camera means after a time delay corresponding to the round-trip propagation time of said light pulses to and from said object;
gating said camera means on one pulse after the leading edge of the reflected light is detected; and converting the detected pulses of non-visible light to a video image of said object.

30. An apparatus for detecting and imaging an object at night or where atmospheric propagation of visible light is severely hampered by fog, dust, smoke, haze or snow comprising:
  generating means for selectively generating pulses of non-visible light;
  projecting means for projecting said pulses of non-visible light at an object at night or where atmospheric propagation of visible light is severely hampered by fog, dust, smoke, haze or snow;
  detecting means for detecting said pulses of light reflected back from said object after a time delay corresponding to the round-trip propagation time of said light pulses to and from said object;
  glint detection means for detecting the leading edge of light reflected back from said object; and
  converting means for converting the detected pulses of non-visible light to a video image of said object.

31. The apparatus of claim 30 wherein said glint detection means comprises:
  fast photodiode means; and
  pulse discriminator means operatively connected to said fast photodiode means.

32. An apparatus for detecting and imaging an object at night or where atmospheric propagation of visible light is severely hampered by fog, dust, smoke, haze or snow comprising:
  generating means for selectively generating pulses of non-visible light;
  projecting means for projecting said pulses of non-visible light at an object at night or where atmospheric propagation of visible light is severely hampered by fog, dust, smoke, haze or snow;
  at least one camera means for detecting said pulses of light reflected back from said object after a time delay corresponding to the round-trip propagation time of said light pulses to and from said object;
  gating means for gating said camera means on one pulse after the leading edge of the reflected light is detected; and
  converting means for converting the detected pulses of non-visible light to a video image of said object.

* * * * *

UNITED STATES PATENT AND TRADEMARK OFFICE
CERTIFICATE OF CORRECTION

PATENT NO. : 5,013,917
DATED : May 7, 1991
INVENTOR(S) : Bobby L. Ulich

It is certified that error appears in the above-identified patent and that said Letters Patent is hereby corrected as shown below:

Col. 6, Row 53    Delete "A=0.096 m." and insert therefore -- $A=0.096m^2$.

Col. 8, Row 46    Delete "that" and insert therefore --than--.

Col. 9, Row 4     Delete "where" and re-insert it after the formula "S=..." and before "E=laser ...".

Col. 9, Row 17    Delete "2.9971 X $10^8$" and insert therefore -- 2.997q X $10^8$ --.

Col. 10, Row 24   Delete "2.9971 X $10^8$" and insert therefore -- 2.997q X $10^8$ --.

Signed and Sealed this

Twentieth Day of July, 1993

Attest:

MICHAEL K. KIRK

*Attesting Officer*     *Acting Commissioner of Patents and Trademarks*